(12) United States Patent
Sawada et al.

(10) Patent No.: US 11,266,429 B2
(45) Date of Patent: Mar. 8, 2022

(54) TRANSDUCER UNIT AND ULTRASONIC TREATMENT INSTRUMENT

(71) Applicant: Olympus Corporation, Hachioji (JP)

(72) Inventors: Kiichiro Sawada, Hachioji (JP); Chikayoshi Meguro, Hachioji (JP)

(73) Assignee: OLYMPUS CORPORATION, Tokyo (JP)

( * ) Notice: Subject to any disclaimer, the term of this patent is extended or adjusted under 35 U.S.C. 154(b) by 42 days.

(21) Appl. No.: 16/745,144

(22) Filed: Jan. 16, 2020

(65) Prior Publication Data

US 2020/0146707 A1 May 14, 2020

Related U.S. Application Data

(63) Continuation of application No. PCT/JP2017/026494, filed on Jul. 21, 2017.

(51) Int. Cl.
*A61B 17/32* (2006.01)

(52) U.S. Cl.
CPC .......... *A61B 17/320068* (2013.01); *A61B 2017/320072* (2013.01)

(58) Field of Classification Search
CPC ........... A46B 5/02; A46B 5/021; A46B 5/023; A46B 5/025; A46B 5/026;
(Continued)

(56) References Cited

U.S. PATENT DOCUMENTS

| 4,739,536 A * | 4/1988 | Bandera ............... | B25G 1/105 16/430 |
| 5,355,552 A * | 10/1994 | Huang ................. | A63B 49/08 16/421 |

(Continued)

FOREIGN PATENT DOCUMENTS

| JP | S58-001660 | 1/1983 |
| JP | H10-511048 | 10/1998 |

(Continued)

OTHER PUBLICATIONS

International Search Report and Written Opinion from corresponding International Application No. PCT/JP2017/026494, dated Jul. 21, 2017.

*Primary Examiner* — Ryan J. Severson
(74) *Attorney, Agent, or Firm* — Oliff PLC

(57) ABSTRACT

The disclosed technology is directed to a transducer unit used in a treatment instrument that comprises an ultrasonic transducer configured to generate ultrasonic vibrations. A cylindrically-shaped casing is configured to hold the ultrasonic transducer therein along a central axis. The cylindrically-shaped casing includes an outer circumferential portion having respective circular arc portions and extension portions formed thereon. A virtual polygon is formed by connecting together a plurality of virtual points located at positions outside of the outer circumferential portion and is separated by a predetermined distance from the central axis when a cross-section intersecting the central axis at right angles and a first virtual distance between the central axis and each side of the virtual polygon are defined. The circular arc portions each includes, as a radius from the central axis, a first length greater than the first virtual distance but smaller than the predetermined distance.

14 Claims, 9 Drawing Sheets

(58) Field of Classification Search
CPC .......... A61B 17/320068; A61B 2017/320072; A61B 2017/320084; A61B 2017/320088; B25G 1/10; B25G 1/102; B25G 1/105; Y10T 16/476

See application file for complete search history.

(56) References Cited

U.S. PATENT DOCUMENTS

| | | | | |
|---|---|---|---|---|
| D360,344 S | * | 7/1995 | Eggert | .............................. D8/83 |
| 5,530,989 A | | 7/1996 | Remmert et al. | |
| 5,722,116 A | * | 3/1998 | Lin | ........................ B25G 1/105 |
| | | | | 16/436 |
| D553,464 S | * | 10/2007 | Rinner | .............................. D8/83 |
| 2018/0132885 A1 | * | 5/2018 | Cotter | ............ A61B 17/320068 |

FOREIGN PATENT DOCUMENTS

| | | |
|---|---|---|
| JP | 2000-271138 | 10/2000 |
| JP | 2001-321388 | 11/2001 |
| JP | 2003-052712 | 2/2003 |
| JP | 2006-081760 | 3/2006 |

* cited by examiner

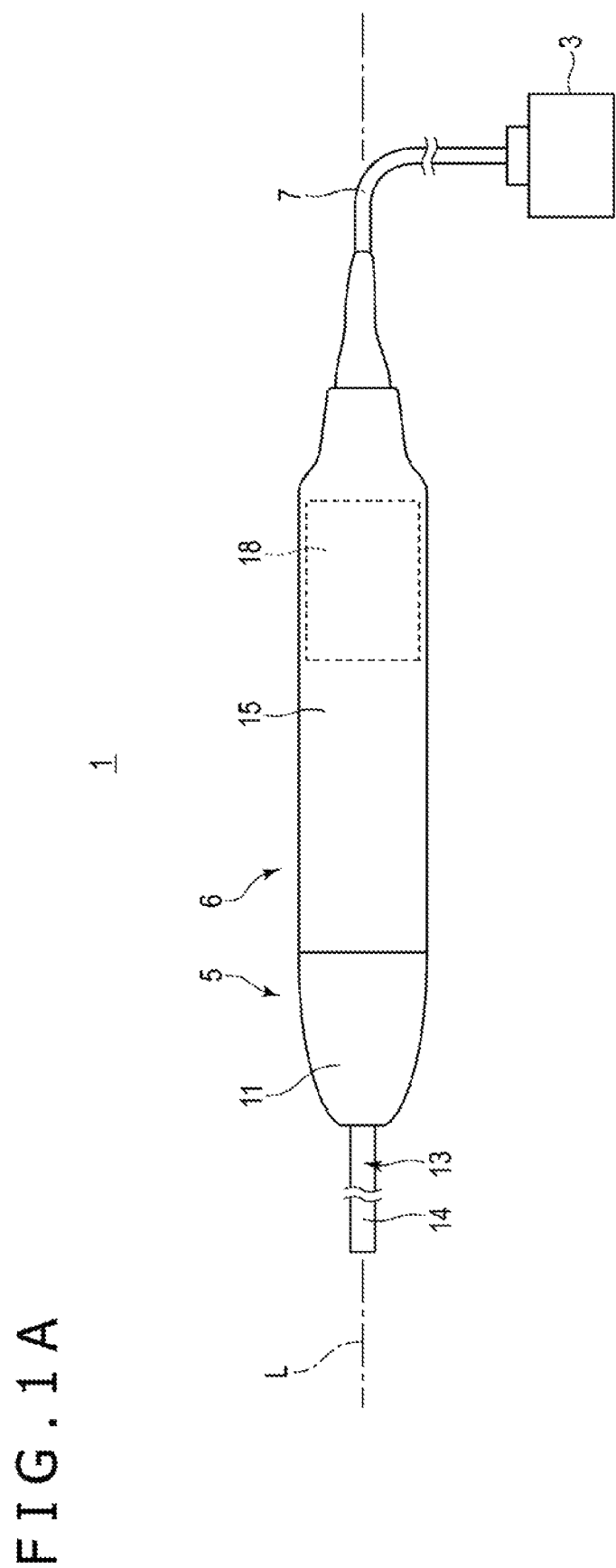

11,266,429 B2

TRANSDUCER UNIT AND ULTRASONIC TREATMENT INSTRUMENT

CROSS-REFERENCE TO RELATED APPLICATION

This application is a continuation application of PCT Application No. PCT/JP2017/026494 filed on Jul. 21, 2017, which is hereby incorporated by reference in its entirety.

TECHNICAL FIELD

The disclosed technology relates to a transducer unit having an ultrasonic transducer and also to an ultrasonic treatment instrument including the transducer unit.

DESCRIPTION OF THE RELATED ART

JP 2003-052712 A discloses an ultrasonic treatment instrument that treats a target of treatment with ultrasonic vibrations. This ultrasonic treatment instrument includes a casing, i.e., an exterior, which is disposed extending along a central axis and is to be held by a surgeon. Inside the casing, an ultrasonic transducer is arranged. The ultrasonic transducer converts supplied electrical energy to ultrasonic vibrations. The resulting ultrasonic vibrations are transmitted to an end effector, i.e., a treatment portion, and are applied from the end effector to a target of treatment.

With an ultrasonic treatment instrument such as that disclosed in JP 2003-052712 A, the smaller the outer diameter of a casing, the easier for a surgeon or a user to grasp it upon treatment. Further, the casing is preferably formed in a shape that is difficult to slip when grasped by the surgeon.

BRIEF SUMMARY OF EMBODIMENTS

The disclosed technology has been made in view of the problem described hereinbefore.

One aspect of the disclosed technology is directed to a transducer unit used in a treatment instrument that comprises an ultrasonic transducer configured to generate ultrasonic vibrations when receiving supply of electrical energy. A cylindrically-shaped casing is configured to hold the ultrasonic transducer therein along a central axis from a distal end to a proximal end. The cylindrically-shaped casing includes an outer circumferential portion having respective circular arc portions and extension portions formed thereon. A virtual polygon is formed by connecting together a plurality of virtual points located at positions outside of the outer circumferential portion and is separated by a predetermined distance from the central axis when a cross-section intersecting the central axis at right angles and a first virtual distance between the central axis and each side of the virtual polygon are defined. The circular arc portions each includes, as a radius from the central axis, a first length greater than the first virtual distance but smaller than the predetermined distance. The extension portions extend at the positions of the virtual points, respectively, over a second length, which is greater than the first length but is smaller than the predetermined distance, as a distance from the central axis. The first length is smaller in terms of the distance from the central axis on a side of the proximal end than on a side of the distal end.

Another aspect of the disclosed technology is directed to a transducer unit used in a treatment instrument that comprises an ultrasonic transducer configured to generate ultrasonic vibrations when receiving supply of electrical energy. A cylindrically-shaped casing is configured to hold the ultrasonic transducer therein along a central axis from a distal end to a proximal end. The cylindrically-shaped casing includes an inner circumference and an outer circumference. The inner circumference includes at least a portion formed from a side of the distal end to a side of the proximal end with a predetermined radius from the central axis when a cross-section intersecting the central axis at right angles. The outer circumference is formed from parts of a polygon with an inscribed circle having a radius of the inner circumference and from parts of a circumference having a greater radius from the central axis on the side of the distal end than on the side of the proximal end. The outer circumference is formed from sides of the polygon if a distance from the central axis to each side of the polygon is greater than the radius of the circumference. The outer circumference is formed from circular arc portions of the circumference if the distance from the central axis to each side of the polygon is not greater than the radius of the circumference.

A further aspect of the disclosed technology is directed to an ultrasonic treatment instrument that comprises a transducer unit having an ultrasonic transducer configured to generate ultrasonic vibrations using supply of electrical energy. The cylindrically-shaped casing to hold the ultrasonic transducer therein along a central axis from a distal end to a proximal end. A treatment unit having an end effector is configured to receive the ultrasonic vibrations. The cylindrically-shaped casing includes an outer circumferential portion having respective circular arc portions and extension portions formed thereon. A virtual polygon is formed by connecting together a plurality of virtual points located at positions outside of the outer circumferential portion and is separated by a predetermined distance from the central axis when a cross-section intersecting the central axis at right angles and a first virtual distance between the central axis and each side of the virtual polygon are defined. The circular arc portions each includes, as a radius from the central axis, a first length greater than the first virtual distance but smaller than the predetermined distance. The extension portions extend at the positions of the virtual points, respectively, over a second length, which is greater than the first length but is smaller than the predetermined distance, as a distance from the central axis. The first length is smaller in terms of the distance from the central axis on a side of the proximal end than on a side of the distal end.

BRIEF DESCRIPTION OF THE DRAWINGS

The technology disclosed herein, in accordance with one or more various embodiments, is described in detail with reference to the following figures. The drawings are provided for purposes of illustration only and merely depict typical or example embodiments of the disclosed technology. These drawings are provided to facilitate the reader's understanding of the disclosed technology and shall not be considered limiting of the breadth, scope, or applicability thereof. It should be noted that for clarity and ease of illustration these drawings are not necessarily made to scale.

FIG. 1A is a view schematically illustrating an ultrasonic treatment instrument according to a first embodiment.

DETAILED DESCRIPTION OF THE EMBODIMENTS

Figure 1B:
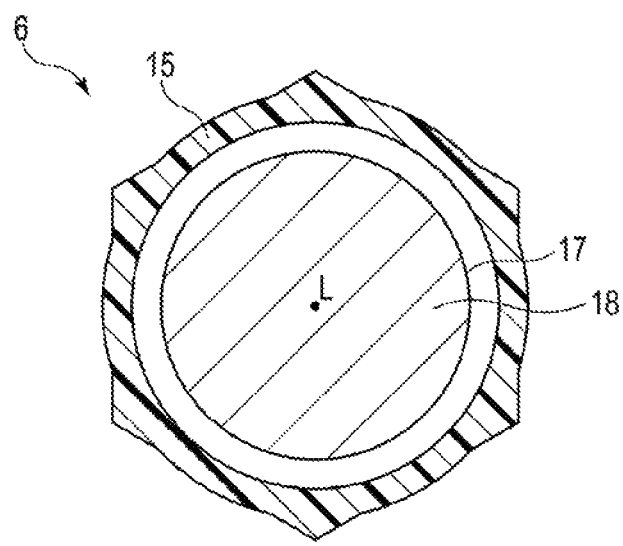
FIG. 1B is a view schematically illustrating a cross-section intersecting at right angles a longitudinal axis of the ultrasonic treatment instrument according to the first embodiment.

In the following description, various embodiments of the technology will be described. For purposes of explanation, specific configurations and details are set forth in order to provide a thorough understanding of the embodiments. However, it will also be apparent to one skilled in the art that the technology disclosed herein may be practiced without the specific details. Furthermore, well-known features may be omitted or simplified in order not to obscure the embodiment being described.

The disclosed technology has as an object thereof the provision of a transducer unit having a casing formed in a shape that is easy to grasp and difficult to slip.

First Embodiment

Referring to FIGS. 1A through 4D, a description will be made about a first embodiment of the disclosed technology.

FIG. 1A is a view illustrating a treatment instrument 1 as an ultrasonic treatment instrument of this embodiment. The treatment instrument 1 of this embodiment is used in treatment including resection of a bone or the like or formation of a hole in or through a bone or the like under an arthroscope by bringing a treatment portion, to which ultrasonic vibrations are being transmitted, into contact with the bone or the like. As illustrated in FIG. 1A, the treatment instrument 1 includes a first connector 5, i.e., a treatment unit, having an end effector 14, i.e., a treatment portion, and a second connector 6, i.e., a transducer unit, detachably attached to the first connector 5. The second connector 6 has a central axis L, i.e., a longitudinal axis, and is disposed extending along the central axis L. Here, a direction along, i.e., substantially parallel to, the central axis L is assumed to be a longitudinal direction, one side in the longitudinal direction is assumed to be a distal end side, and the side opposite to the distal end side is assumed to be a proximal end side. When using the treatment instrument 1, the first connector 5 and the second connector 6 are connected together at a proximal end thereof and a distal end thereof, respectively. In an example, the first connector 5 is disposed of after use of the treatment instrument 1. After using the treatment instrument 1, the second connector 6 is subjected to irrigation, disinfection, sterilization, and the like, and is then reused.

The first connector 5 includes a casing 11. At the first connector 5, a rod member 13, i.e., a probe, is disposed extending along the central axis L from an inside of the casing 11 toward the distal end side. The rod member 13 is supported by the casing 11. The rod member 13 is formed from a material having electrical conductivity and high vibration transmissivity, for example, a titanium alloy or the like. A distal end portion of the rod member 13 projects from a distal end of the casing 11 toward the distal end side. By a projecting portion of the rod member 13 from the casing 11, the end effector 14 which treats a target of treatment is formed.

The second connector 6 includes a casing 15, i.e., handpiece. The casing 15 forms, at an outer surface thereof, an exterior, i.e., an outer surface, of the second connector 6. The casing 15 is formed in a substantially cylindrical shape. The casing 15 opens toward the distal end side at a distal end portion thereof. The casing 15 is formed, for example, with a resin material such as polyphenylsulfone. To the casing 15, a cable 7 is connected at one end thereof. The cable 7 is detachably connected at an opposite end thereof to a power source device 3. The power source device 3 supplies electrical energy to the treatment instrument 1 to actuate the treatment instrument 1.

As illustrated in FIGS. 1A and 1B, a transducer casing 17 is arranged inside the casing 15. The transducer casing 17 internally includes an ultrasonic transducer 18. The ultrasonic transducer 18 includes ultrasonic transducer elements and a vibration transmitting member. The ultrasonic transducer elements convert electrical energy to vibration energy, whereby ultrasonic vibrations are generated. The ultrasonic vibrations generated at the ultrasonic transducer elements are transmitted to the vibration transmitting member. In addition, inside the casing 15, the rod member 13 and the vibration transmitting member of the ultrasonic transducer 18 are connected together at a proximal end thereof and a distal end thereof, respectively.

At the transducer casing 17, a predetermined clearance is formed between the transducer casing 17 and the ultrasonic transducer 18 to suppress effects of heat caused by ultrasonic vibrations. At the transducer casing 17, a cross-section, which intersects the central axis L at right angles, i.e., substantially perpendicularly, is formed in a substantially circular shape for diameter reduction. The casing 15 preferably has an inner diameter, i.e., an inner circumferential surface, formed slightly greater than an outer diameter of the transducer casing 17 for diameter reduction.

The power source device 3 includes an unillustrated ultrasonic power supply. The ultrasonic power supply is electrically connected to the ultrasonic transducer elements of the ultrasonic transducer 18 via an unillustrated electrical pathway laid extending through an inside of the cable 7 and the inside of the casing 15 of the connector 6. The ultrasonic electric power supply includes a waveform generator, a conversion circuitry, a transformer, and the like, and converts electrical power from a battery electrical source, a commercial power outlet, or the like to an ac power of, for example, any frequency in a predetermined frequency range. The ultrasonic power supply supplies the converted ac power to the ultrasonic transducer 18. By the supply of the electrical energy to the ultrasonic transducer 18, ultrasonic vibrations are generated at the ultrasonic transducer 18. The ultrasonic vibrations generated at the ultrasonic transducer 18 are transmitted to the end effector 14 via the rod member 13. The transmitted ultrasonic vibrations are then applied to the target of treatment from the end effector 14.

Figure 2:
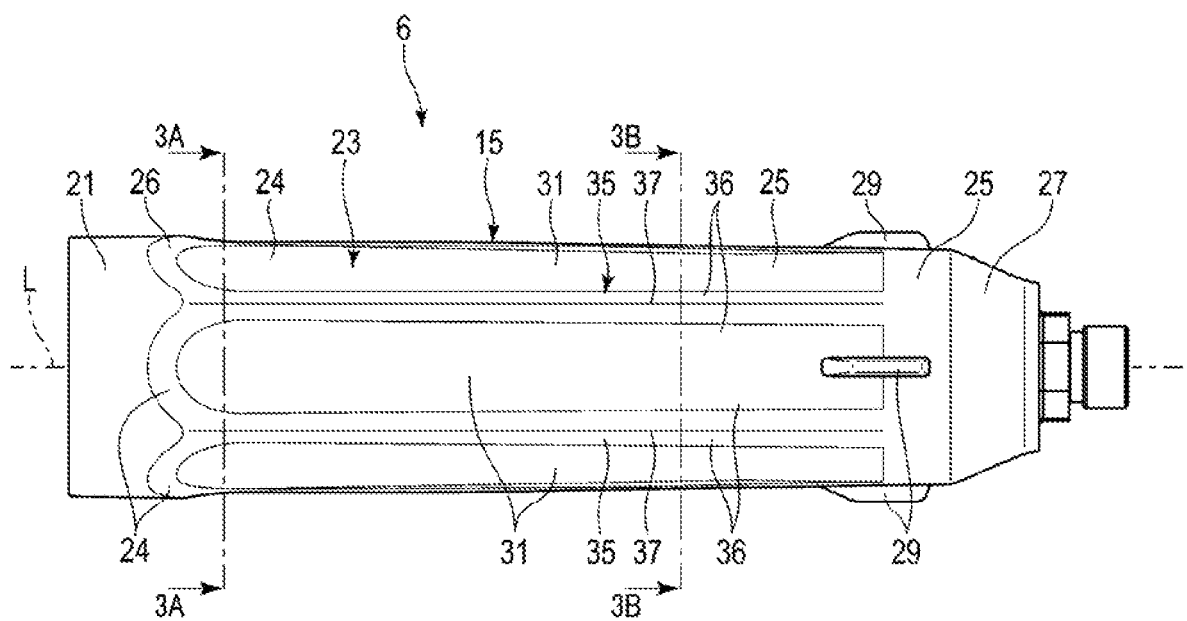
FIG. 2 is a view schematically illustrating a casing in the first embodiment.

Next, as illustrated in FIG. 2, the casing 15 includes a connecting portion 21, a casing main body 23, and a cable connecting portion 27. The connecting portion 21 is connected to the first connector 5. The casing main body 23 is disposed extending from the connecting portion 21 toward the proximal end side. The cable connecting portion 27 is disposed on the proximal end side of the casing main body 23. The connecting portion 21 forms the distal end portion of the casing 15. Further, the cable connecting portion 27 forms a proximal end portion of the casing 15, and the cable 7 described hereinbefore is connected at the one end thereof to the cable connecting portion 27.

The casing main body 23 is disposed between the connecting portion 21 and the cable connecting portion 27 as viewed in the longitudinal direction. The casing main body 23 is formed on the assumption that it will be held by a surgeon in treatment. The casing main body 23 is recessed inward at a distal end thereof relative to a proximal end of the connecting portion 21 as viewed in a radial direction about the central axis L. Between the distal end of the casing main body 23 and the proximal end of the connecting portion 21, a sloping portion 26 is therefore formed directed progressively inward as viewed in the radial direction from the distal end side toward the proximal end side.

On an outer circumferential surface of the casing 15, rib portions 29 are disposed. The rib portions 29 protrude outward in the radial direction from the outer circumferential surface of the casing 15. The rib portions 29 are disposed on or in a vicinity of a proximal end side portion 25 of the casing main body 23. In this embodiment, the rib portions 29 are disposed as many as four on the casing 15. The rib portions 29 are arranged at equal intervals in a circumferential direction of the casing 15, in other words, about the central axis L.

Figure 3A:
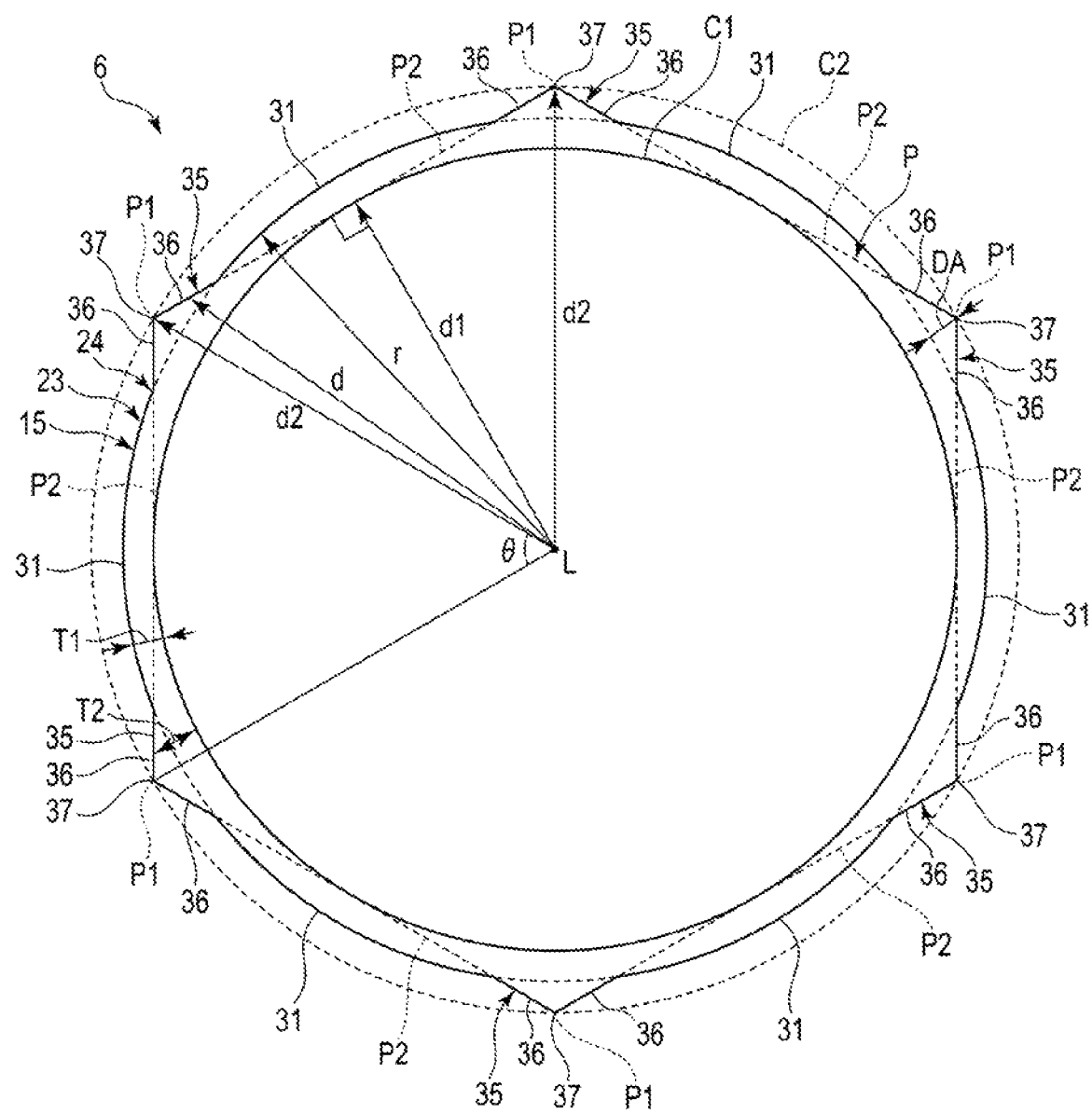
FIG. 3A is a view schematically illustrating a 3A-3A cross-section of FIG. 2.
Figure 3B:
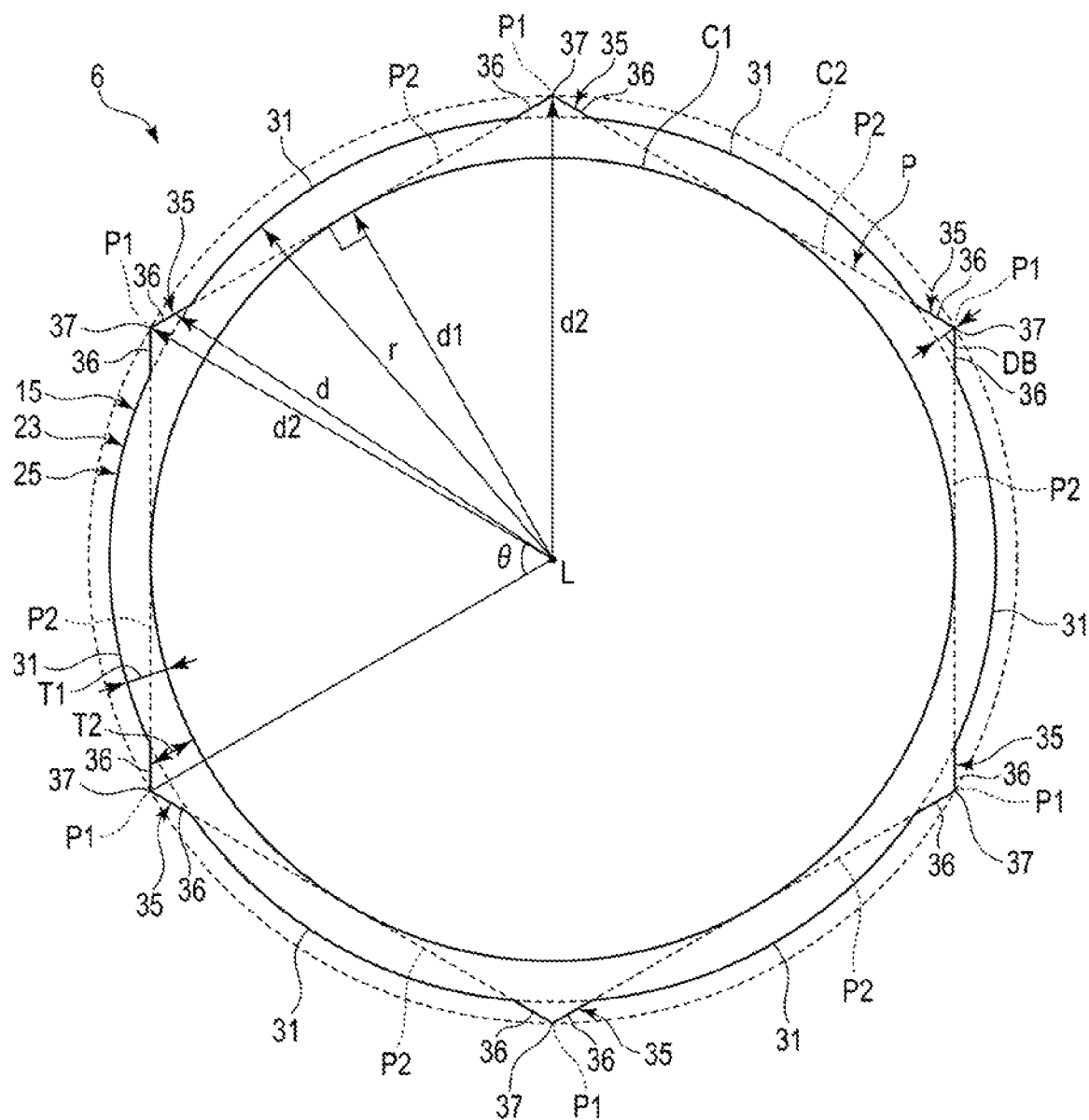
FIG. 3B is a view schematically illustrating a 3B-3B cross-section of FIG. 2.

As illustrated in FIGS. 3A and 3B, the casing main body 23 includes circular arc portions 31 and extension portions 35. In a cross-section crossing, i.e., intersecting, the central axis L at right angles, the circular arc portions 31 form at outer circumferential surfaces thereof circular arc shapes about the central axis L, and the extension portions 35 have outer circumferential surfaces located outward, i.e., outside, in the radial direction relative to the circular arc portions 31. The circular arc portions 31 and extension portions 35 are all arranged extending along the longitudinal direction. The circular arc portions 31 and extension portions 35 are arranged alternately in the circumferential direction of the casing 15. Accordingly, the number of the circular arc portions 31 and the number of the extension portions 35 are equal. On an outer circumferential surface of the casing main body 23, each extension portion 35 is arranged between the adjacent two circular arc portions 31, and each circular arc portion 31 is arranged between the adjacent two extension portions 35, as viewed in the circumferential direction of the casing 15. The casing main body 23 is formed by the circular arc portions 31 and extension portions 35 over the entire circumference thereof about the central axis L.

In this embodiment, the circular arc portions 31 are disposed as many as six, and so are the extension portions 35, on the outer circumferential surface of the casing main body 23. The extension portions 35 are formed in substantially the same shape, relative to each other. The circular arc portions 31 and extension portions 35 are disposed at equal intervals, in the circumferential direction of the casing 15, in other words, about the central axis L.

The extension portions 35 each include two planar portions 36 and a ridge portion 37 formed between the two planar portions 36. Each ridge portion 37 is formed at a middle position of the corresponding extension portion 35 as viewed in the circumferential direction of the casing 15, in other words, about the central axis L. Each ridge portion 37 forms a ridge of the corresponding extension portion 35. The ridge of the extension portion 35 is arranged extending along the longitudinal direction.

Now, a virtual hexagon P, i.e., polygon, with the central axis L as a center will be defined in a cross-section of the casing main body 23, the cross-section intersecting the central axis L at right angles. In this embodiment, the hexagon P is a regular hexagon. In FIGS. 3A and 3B, the hexagon P is presented by a broken line. The polygon P has six angles P1 and six sides P2. Each side P2 is located between the adjacent angles P1, and each angle P1 is located between the adjacent sides P2. In other words, the hexagon P is a polygon formed by connecting a plurality of, i.e., at least three, virtual points (P1) which are separated by a predetermined distance from the central axis L.

Each angle P1 is located at an angular position separated by 60° from each of the adjacent angles P1 about the central axis L. Further, a distance d2 between each angle P1 and the central axis L has the same value as a radius of a circumscribed circle C2 of the hexagon P. Each angle P1 is defined at a position separated by a predetermined distance (d2) from the central axis L. The distance d1, i.e., a first virtual distance, between each side P2 and the central axis L has the same value as a radius of an inscribed circle C1 of the hexagon P. The distance d2, i.e., the second virtual distance, between each angle P1 and the central axis L is greater than the distance d1 between each side P2 and the central axis L. In addition, each side P2 is located over the entirety thereof between the inscribed circle C1 and the circumscribed circle C2 as viewed in the radial direction.

In the cross-section intersecting the central axis L at right angles, the circular arc portions 31 are each located between the inscribed circle C1 and the circumscribed circle C2 of the hexagon P. The length from the central axis L to each circular arc portion 31, in other words, a radius r from the central axis L to each circular arc portion 31, is thus greater than the radius d1 of the inscribed circle C1 but smaller than the radius d2 of the circumscribed circle C2.

The extension portions 35 each extend outward in the radial direction relative to the adjacent circular arc portions 31. The distance d from the central axis L to each extension portion 35 is therefore greater than the radius r of each circular arc portion 31. In other words, the length d from the central axis L to each extension portion 35 is greater than the radius d1 of the inscribed circle C1.

The ridge portions 37 of the extension portions 35 are located at the same or substantially the same angular positions as the angles P1 of the hexagon P as viewed in the circumferential direction of the casing 15, in other words, about the central axis L. Further, in the cross-section intersecting the central axis L at right angles, lines formed by the planar portions 36 of each extension portion 35 are located on the corresponding sides P2, respectively, of the hexagon P. Accordingly, the angle between the two planar portions 36 in each extension portion 35 is approximately 120°.

Each planar portion 36 is located between the inscribed circle C1 and the circumscribed circle C2 of the hexagon P as viewed in the radial direction. The length d between the extension portion 35 in each planar portion 36 and the central axis L is greater than the radius d1 of the inscribed circle C1 but smaller than the radius d2 of the circumscribed circle C2. In the cross-section intersecting the central axis L at right angles, the ridge portion 37 of each extension portion 35 is formed at substantially the same position as the corresponding angle P1 of the hexagon P. Therefore, the length d between the extension portion 35 at each ridge portion 37 and the central axis L has substantially the same value as the radius d2 of the circumscribed circle C2.

Since the circular arc portions 31 and extension portions 35 have the configurations as described hereinbefore, the extension portions 35 are formed along the virtual hexagon P in the cross-section intersecting the central axis L at right angles. Hence, the length d between each extension portion 35 and the central axis L is greater than the radius r of each circular arc portion 31 but not greater than the radius d2 of the circumscribed circle C2. Further, the cross-sectional area formed by the outer circumferential surface of the casing 15 in the casing main body 23 is greater than the area of a circle having a radius equal to the radius r of each circular arc portion 31 and the area of the inscribed circle C1 but smaller than the area of the circumscribed circle C2.

In this embodiment, the inner circumferential surface of the casing main body 23 is disposed extending, for example, along the inscribed circle C1. The casing main body 23 therefore has, at each extension portion 35, a wall thickness T2 (d–d1) greater than a wall thickness T1 (r–d1) of the casing main body 23 at each circular arc portion 31. In an example, the casing 15 is fabricated by injection molding, with the inner circumferential surface of the casing main body 23 being formed in substantially the same shape as the outer circumferential surface of the casing main body 23. In this case, the wall thickness T2 (d–d1) of the casing main body 23 at each extension portion 35 is substantially the same as the wall thickness T1 (r–d1) of the casing main body 23 at each circular arc portion 31, whereby the casing main body 23 can be formed with a substantially uniform wall thickness.

In the casing main body 23, the extension length (d–r) of each extension portion 35 from each of the adjacent circular arc portions 31 as viewed in the radial direction becomes smaller from the distal end side toward the proximal end side at substantially the same angular position as viewed about the central axis L. At a first position (see FIG. 3A) located on a distal end side portion 24 of the casing main body 23, for example, the extension length of each extension portion 35 from each of the adjacent circular arc portions 31 is a first length DA. At a second position (see FIG. 3B) located on the proximal end portion 25 of the casing main body 23 and located closer to the proximal end side than the first position, on the other hand, the extension length of each extension portion 35 from each of the adjacent circular arc portions 31 is a second length DB smaller than the first length DA.

In another example, the radius r of each circular arc portion 31 is formed progressively smaller from the distal end side toward the proximal end side to facilitate the formation of the casing 15.

A description will next be made about operations and advantageous effects of the treatment instrument 1. The treatment instrument 1 of this embodiment is, for example, used in treatment including resection of a body tissue such as a bone or formation of a hole in or through a body tissue such as a bone. Upon performing the treatment with the treatment instrument 1, the surgeon holds the casing 15 of the second connector 6, and with the end effector 14 placed in a vicinity of a target of treatment, inputs an operation to cause output of electrical energy from the power source device 3 to the treatment instrument 1. By supply of electrical energy to the ultrasonic transducer 18 of the treatment instrument 1, ultrasonic vibrations, i.e., longitudinal vibrations, generated at the ultrasonic transducer 18 are transmitted to the end effector 14 as described hereinbefore. In addition, by rotating and moving the treatment instrument 1 back and forth relative to the target of treatment such as a bone, the end effector 14 is brought, in a desired posture, into contact with the target of treatment. By moving the treatment instrument 1, for example, along the longitudinal direction with ultrasonic vibrations being transmitted to the end effector 14, the treatment with ultrasonic vibrations as described hereinbefore is performed.

In the treatment described hereinbefore, the surgeon may change the manner of holding, i.e., the manner of grasping, the treatment instrument 1, according to the conditions of the treatment or the kind of the treatment. FIGS. 4A to 4D illustrate examples of the manner of holding when the surgeon holds the treatment instrument 1. FIGS. 4A to 4D illustrate how the surgeon holds the treatment instrument 1 in a right hand H0.

Figure 4A:
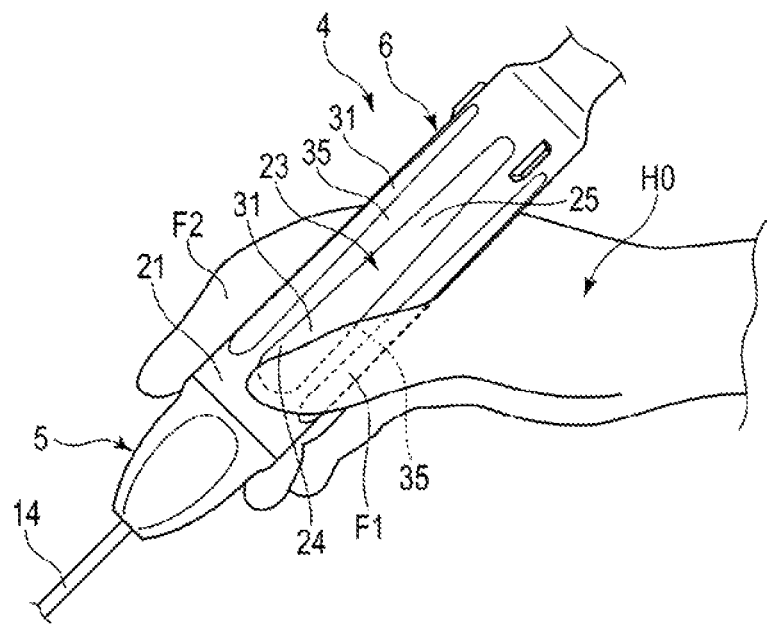
FIG. 4A is a view schematically illustrating an example of how to grasp the ultrasonic treatment instrument according to the first embodiment in treatment with the ultrasonic treatment instrument.

As illustrated in FIG. 4A, for example, the treatment instrument 1 is held like holding a pen or a pencil. In this case, the proximal end side portion 25 of the casing main body 23 of the casing 15 is arranged at a position, i.e., near the webbing, between a thumb F1 and an index finger F2. The thumb F1 and the index finger F2 are then placed on the outer surface of the casing main body 23 with the thumb F1 and the index finger F2 extending from the proximal end side toward the distal end side on the outer surface of the casing main body 23. The casing main body 23 is then held at the distal end portion 24 thereof by the tips of the thumb F1, the index finger F2, and a middle finger F3. With the treatment instrument 1 held as described hereinbefore, treatment is performed by moving the treatment instrument 1 relative to a target of treatment.

Figure 4B:
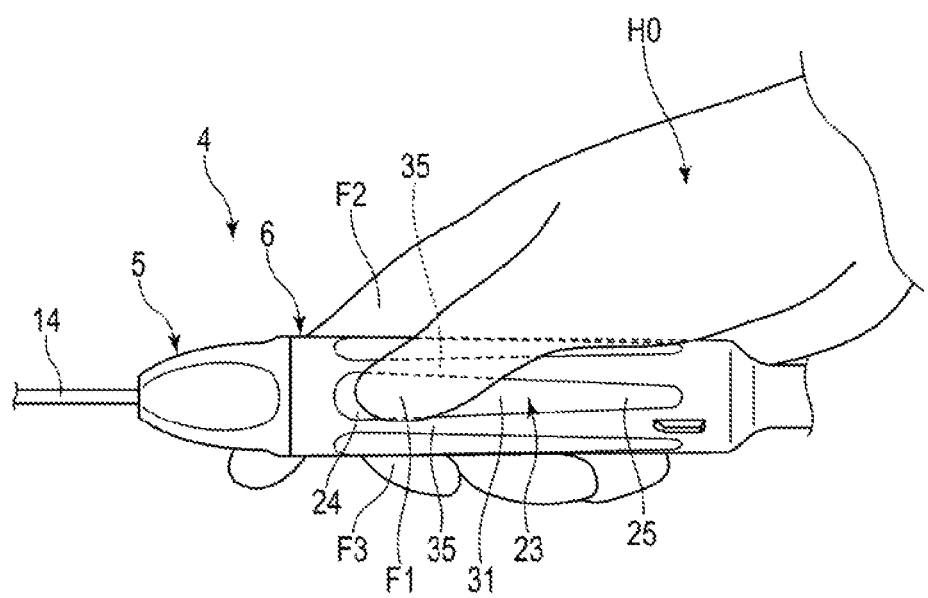
FIG. 4B is a view schematically illustrating another example of how to grasp the ultrasonic treatment instrument according to the first embodiment in treatment with the ultrasonic treatment instrument.
Figure 4C:
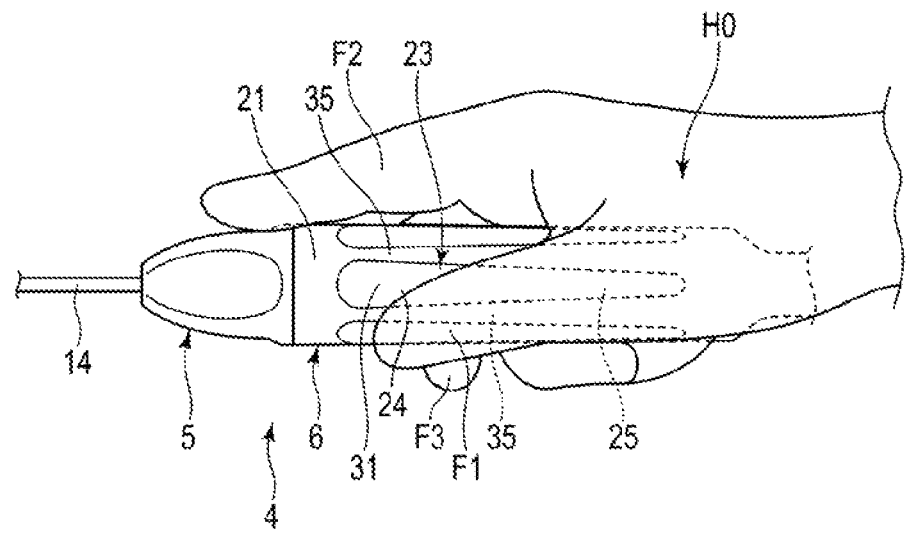
FIG. 4C is a view schematically illustrating a further example of how to grasp the ultrasonic treatment instrument according to the first embodiment in treatment with the ultrasonic treatment instrument.

In the examples illustrated in FIGS. 4B and 4C, the treatment instrument 1 is held like being grasped in the whole hand H0, and is also held at the distal end portion 24 of the casing main body 23 by the tips of the thumb F1, the index finer F2, and the middle finger F3.

Figure 4D:
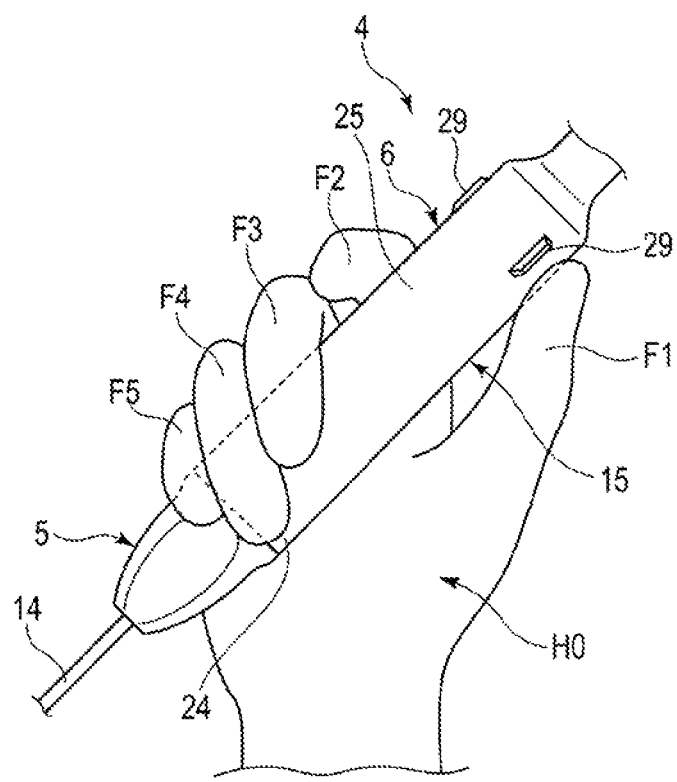
FIG. 4D is a view schematically illustrating a yet further example of how to grasp the ultrasonic treatment instrument according to the first embodiment in treatment with the ultrasonic treatment instrument.

In the example illustrated in FIG. 4D, the treatment instrument 1 is grasped at the distal end side portion 24 of the casing main body 23 between the fingers other than the thumb F1 and the palm, and the thumb F1 is placed on the outer surface of the distal end side portion 25 of the casing main body 23 with the thumb F1 extending from the distal end side toward the proximal end side. In this case, the distal end side portion 24 of the casing main body 23 is held, for example, by the middle finger F3, a ring finger F4, and a little finger F5.

With the treatment instrument 1, the smaller the portion to be grasped by the surgeon, the easier for the surgeon to grasp. Preferably, the casing main body 23 is hence formed with a small radius. The shape of the casing main body 23, especially the size and shape of the inner circumferential surface of the casing main body 23 about the central axis L are defined by the outer diameter of the transducer casing 17 housed in the casing 15. To form the casing main body 23 small, the cross-sectional shapes of the transducer casing 17 and casing main body 23 are preferably formed substantially circular. In addition, the clearance between the transducer casing 17 and the casing main body 23 is preferably formed at a minimum.

As treatment with the treatment instrument 1, the treatment described hereinbefore may be performed with a joint cavity filled with perfusate or the like, on the other hand. In this case, a surgeon holds the casing main body 23 with the outer surface of the casing 15 and the hand H0 wet. The casing main body 23 to be held by the surgeon is preferably formed in a polygonal shape in cross-section for the prevention of slipping. With the treatment instrument 1 in particular, the cross-sectional shape of the casing main body 23 may preferably be formed in a substantially regular hexagonal shape for the prevention of slipping.

In this embodiment, the radius r of each circular arc portion 31 is defined by a half of the outer diameter of the transducer 17, and is formed at a length substantially equal to the half of the outer diameter of the transducer casing 17 or slightly greater than the half of the outer diameter of the transducer casing 17. At the circular arc portions 31, the casing main body 23 is therefore formed in a shape that allows to arrange the transducer casing 17 inside and has a smallest radius.

In this embodiment, the casing main body 23 includes the extension portions 35 extending outward in the radial direction from the adjacent circular arc portions 31. In a cross-section substantially perpendicular to the central axis L, the extension portions 35 are formed in shapes along the virtual hexagon P defined by the ridge portions 37. In other words, the extension portions 35 are portions formed in shapes that include the angles of a regular hexagon. The surgeon can easily suppress the casing main body 23 from slipping in the hand H0 by catching the extension portions 35 with the fingers at the distal end side portion 24 of the casing main body 23. As the extension portions 35 are disposed extending along the longitudinal direction, the treatment instrument 1 is suppressed from slipping in the surgeon's hand H0 especially in the circumferential direction that intersects the longitudinal direction at right angles. As described hereinbefore, the disposition of the portions, which extend outward relative to the adjacent circular arc portions 31, on the outer circumferential surface of the casing main body 23 allows the surgeon to prevent the treatment instrument 1 from slipping in the hand without strongly grasping the treatment instrument 1, whereby the surgeon's hand fatigue in treatment is reduced.

In this embodiment, the casing main body 23 is formed to satisfy the dimensional correlations described hereinbefore, so that the extension portions 35 and the circular arc portions 31 are arranged alternately on the outer circumferential surface of the casing main body 23 as viewed in the circumferential direction. In the treatment instrument 1 of this embodiment, the outer circumferential surface of the casing main body 23 to be held by the surgeon can therefore be formed in a shape that has as small a radius as possible and effectively suppresses slipping in the surgeon's hand. As a consequence, the treatment instrument 1 can be provided satisfying both grasping ease and slipping difficulty.

The extension portions 35 are formed on an outer side than the circular arc portions 31 as viewed in the radial direction. The wall thickness T2 of the casing 15 at each extension portion 35 can therefore be formed greater than the wall thickness T1 of the casing 15 at each circular arc portion 31. As a consequence, the casing 15 is ensured to have wall thicknesses equal to or greater than the wall thickness T1 so that its strength remains appropriate. The casing 15 therefore exhibits grasping ease and slipping difficulty for the surgeon's hand H0 while maintaining strength without an enlargement of its outer diameter as much as possible.

In the example illustrated in FIG. 4A, for example, a portion of the hand H0, the portion being irrelevant to an operation such as a portion near the webbing, for example, comes into contact with the proximal end side portion 25 of the casing main body 23. In this embodiment, at the proximal end side portion 25, the hexagon P is smaller while sharing the common central axis L, and the extension length (d−r) of each extension portion 35 is smaller, compared with those at the distal end side portion 24. Effects on the portion of the surgeon's hand, the portion being irrelevant to an operation, are therefore suppressed. Further, the extension portions 35 are formed so that the extension length (d−r) of each extension portion 35 becomes gradually smaller from the distal end side toward the proximal end side. In other words, the cross-sectional shape of the casing main body 23 is formed so that it gradually becomes closer to a circular shape from the distal end side toward the proximal end side. As a consequence, the effects on the portion of the surgeon's hand, the portion being irrelevant to an operation, are further suppressed.

On the outer circumferential surface of the casing 15, the sloping portion 26 is formed sloping toward the proximal end side relative to the outer surface of the casing main body 23. When the surgeon's fingers come into contact with the sloping portion 26 from the proximal end side, slipping is therefore suppressed between the treatment instrument 1 and the surgeon's hand H0 as viewed in the longitudinal direction.

The rib portions 29 are disposed on the proximal end side portion 25 of the casing main body 23. When the thumb F1 is placed on the proximal end side portion 25 of the casing main body 23, for example, as in the example illustrated in FIG. 4D, slipping between the treatment instrument 1 and the surgeon's hand H0 can therefore be suppressed by bringing the thumb F1 into contact with one of the rib portions 29. Or, the surgeon can easily rotate the treatment instrument 1 by catching one or successively two or more of the rib portions 29 with the thumb F1. The four rib portions 29 are separated by 90° from each other about the central axis L of the casing 15. Of the rib portions 29, the paired rib portions 29 separated by 180° from each other about the central axis L are located, on or in the vicinity of the proximal end portion 25 of the casing main body 23, for example, on the proximal end side of positions along which the corresponding angles P1 are formed, respectively. The remaining paired rib portions 29 are separated by 180° from each other about the central axis L, and are located, on or in the vicinity of the proximal end portion 25 of the casing main body 23, for example, on the proximal end side of a position between two adjacent ones of the remaining four angles P1 and a position between the remaining two adjacent angles P1, along the central axis L. If the four rib portions 29 are arranged relative to the hexagon P as described hereinbefore, the casing 15 can present a better external appearance compared with other arrangements.

Second Embodiment

Figure 5A:
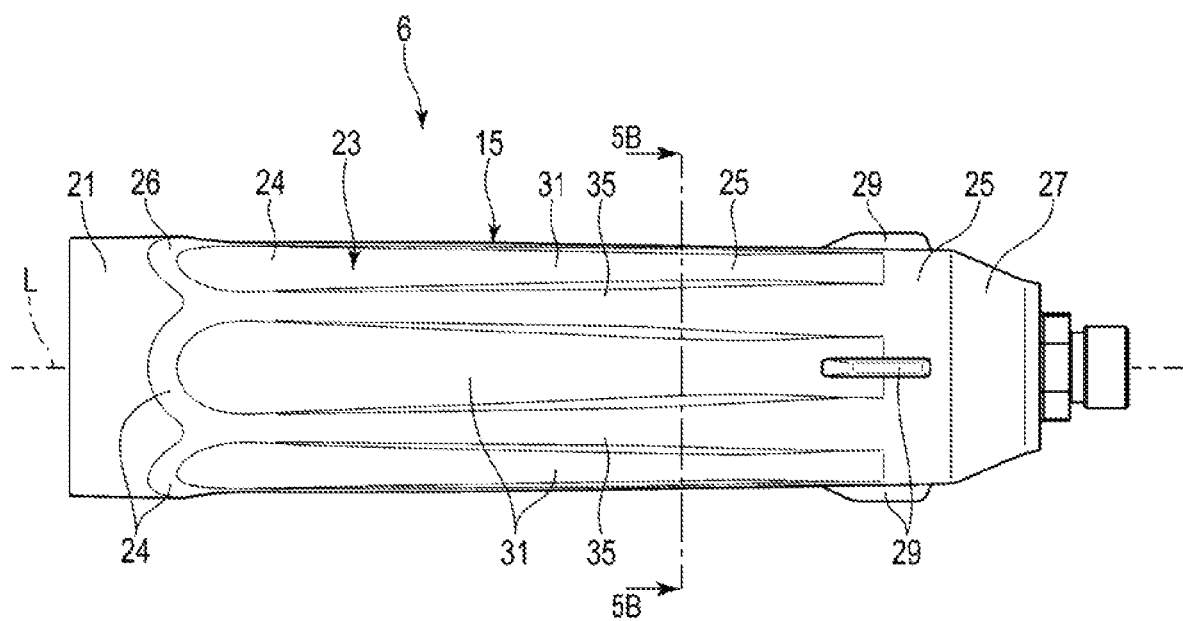
FIG. 5A is a view schematically illustrating a casing in a second embodiment.
Figure 5B:
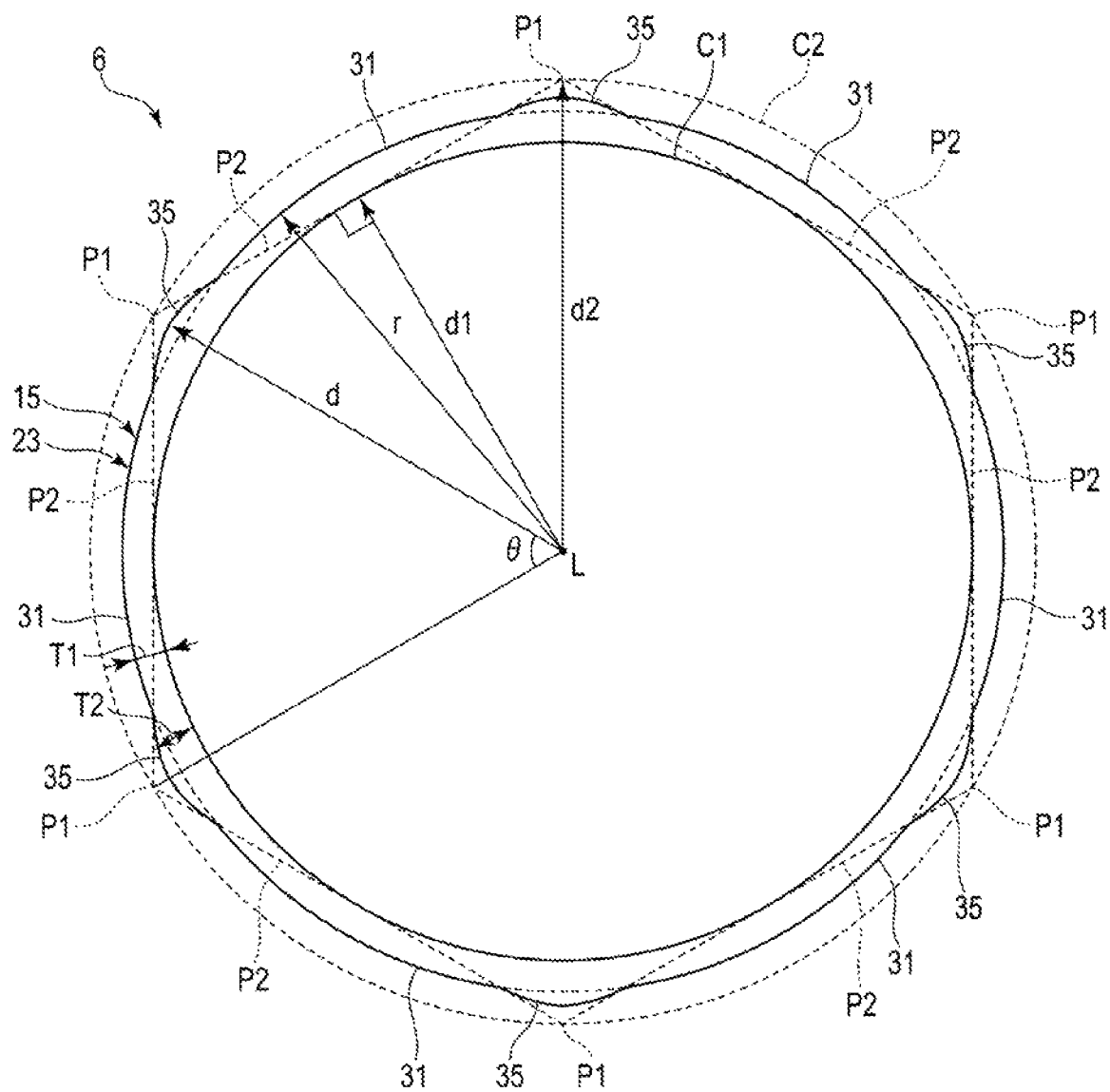
FIG. 5B is a view schematically illustrating a 5B-5B cross-section of FIG. 5A.

Referring to FIGS. 5A and 5B, a description will be made about a second embodiment of the disclosed technology. As the second embodiment, the configuration of the first embodiment has been modified as described hereinafter. Identical elements as in the first embodiment are identified by like reference signs, and their description is omitted.

Extension portions 35 do not need to be formed along the angles P1 of the virtual hexagon P. As illustrated in FIGS. 5A and 5B, each extension portion 35 in this embodiment is formed in a shape that the corresponding angle P1 of the hexagon P has been trimmed at a corner thereof. Each extension portion 35 may also be formed in a shape that the corresponding angle P1 of the hexagon P is rounded. Each extension portion 35 in this embodiment is a curved surface disposed extending along the central axis L.

In this embodiment, the distance d between each extension portion 35 and the central axis L is greater than the radius r of each of the adjacent circular arc portions 31, but is smaller than the radius d2 of the circumscribed circle C2. The circular arc portions 31 and the extension portions 35 are arranged alternately in the circumferential direction of the casing 15. In this embodiment as well, a surgeon can therefore suppress slipping of the casing main body 23 in the hand H0 with ease by catching the extension portions 35 with the fingers at the distal end side portion 24 of the casing main body 23. In addition, the outer circumferential surface of the casing main body 23 to be held by the surgeon can be formed in a shape that has as small a radius as possible and effectively suppresses slipping in the surgeon's hand.

In this embodiment as well, the wall thickness T2 of the casing 15 at each extension portion 35 can be formed greater than the wall thickness T1 of the casing 15 at each circular arc portion 31. As a consequence, the strength of the casing 15 remains appropriate.

In this embodiment, each extension portion 35 is formed in the shape that the corresponding angle P1 of the hexagon P has been trimmed at the corner thereof. Even when the surgeon grasps the extension portions 35, the extension portions 35 can therefore be easily gasped without hurting the hand.

Modifications of Second Embodiment

Figure 6:
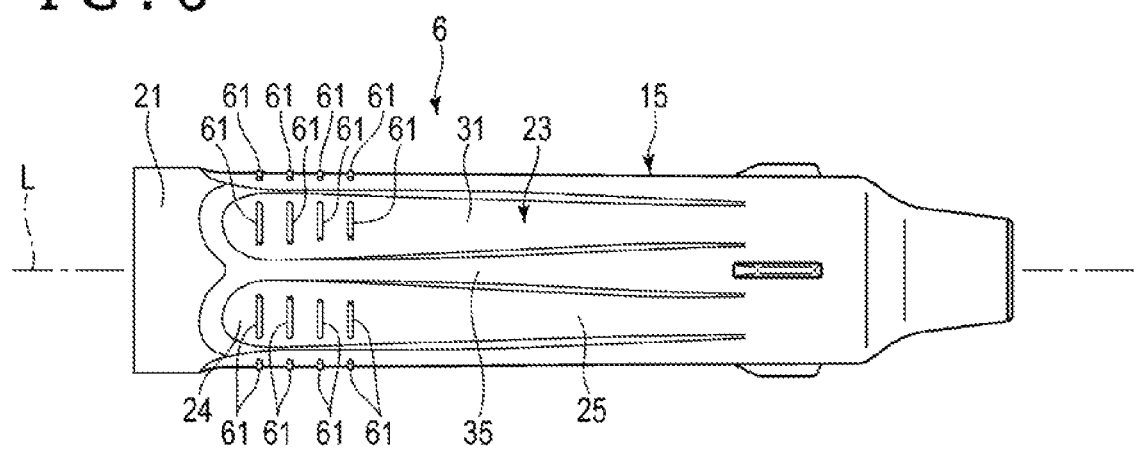
FIG. 6 is a view schematically illustrating a casing in a first modification of the second embodiment.
Figure 7:
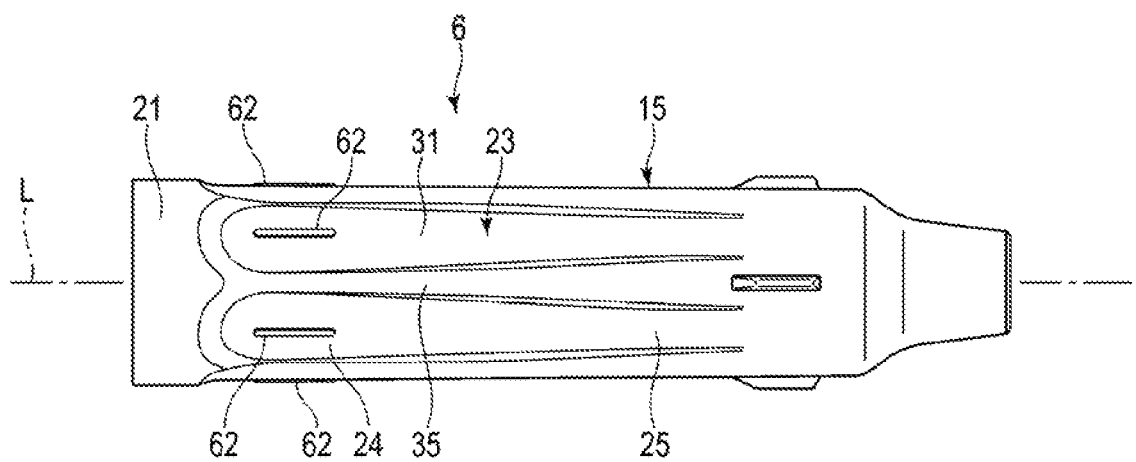
FIG. 7 is a view schematically illustrating a casing in a second modification of the second embodiment.
Figure 8:
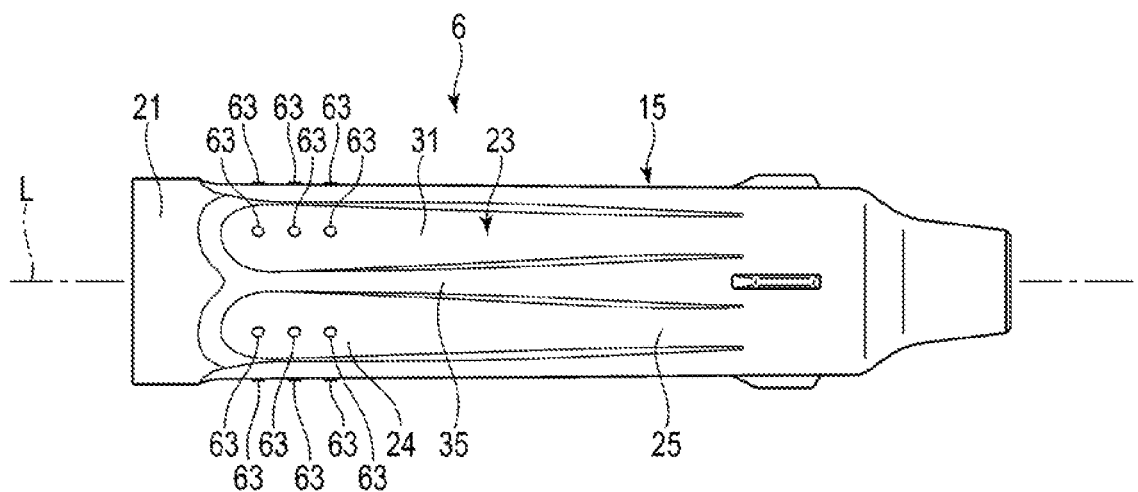
FIG. 8 is a view schematically illustrating a casing in a third modification of the second embodiment.

FIGS. 6 to 8 illustrate modifications of the second embodiment, respectively. In the modification illustrated in FIG. 6, the circular arc portions 31 of the casing main body 23 each include a plurality of rib portions 61. The rib portions 61 each protrude outward relative to the corresponding circular arc portion 31 as viewed in the radial direction. Further, the rib portions 61 are each disposed extending along the circumferential direction. The rib portions 61 on each circular arc portion 31 are arranged at intervals from each other as viewed in the longitudinal direction. The surgeon brings at least one finger into contact with at least one rib 61 in treatment, whereby slipping can be suppressed in the longitudinal direction between the treatment instrument 1 and the surgeon's hand H0.

In the modification illustrated in FIG. 7, a rib 62 is disposed on each circular arc portion 31 of the casing main body 23. The rib portions 62 each protrude outward relative to the corresponding circular arc portion 31 as viewed in the radial direction. The rib portions 62 are each disposed extending substantially in parallel to the central axis L, in other words, extending along the longitudinal direction. The surgeon brings at least one finger into contact with at least one rib 61 in treatment, whereby slipping can be suppressed in the circumferential direction between the treatment instrument 1 and the surgeon's hand H0.

In the modification illustrated in FIG. 8, a plurality of bead portions 63 is disposed on each circular arc portion 31 of the casing main body 23. The bead portions 63 each protrude outward relative to the corresponding circular arc portion 31 as viewed in the radial direction. Further, the bead portions 63 are each formed in a substantially circular shape in the cross-section intersecting the radial direction at right angles. The surgeon brings at least one finger into contact with at least one bead 63 in treatment, whereby slipping can be suppressed in the circumferential direction and/or the longitudinal direction between the treatment instrument 1 and the surgeon's hand H0.

By disposing at least one of the rib portions 61, the rib portions 62, or the bead portions 63, which are described hereinbefore, on each circular arc portion 31 in addition to forming the casing main body 23 as described hereinbefore, slipping of the treatment instrument 1 in treatment can be suppressed more effectively.

In the embodiments and the like described hereinbefore, the extension portions 35 are disposed as many as six on the casing 15, and the extension portions 35 are defined by the virtual hexagon P. However, the disclosed technology is not limited to these configurations. For example, the casing 15 may include eight extension portions 35 defined by a virtual octagon centering around the central axis L. In other words, a polygon which defines extension portions 35 needs to include three or more angles, but does not need to be a regular polygon. The number of angles which a polygon has is adjusted to an appropriate number according to the outer diameter of the transducer casing 17, the outer diameter of the casing 15, and the like.

In the embodiments and the like described hereinbefore, the casing main body 23 is formed by the circular arc portions 31 and extension portions 35 over the entire circumference about the central axis L, but the disclosed technology is not limited to this configuration. The casing main body 23 may include one or more portions, which have a shape different from the circular arc portions 31 or the extension portions 35, on the outer circumferential surface.

Common Configuration of Embodiments and the Like

A transducer unit (6) including a hand-holdable casing (15) disposed extending along a central axis (L) and an ultrasonic transducer (18) that is arranged in the casing (15) and generates ultrasonic vibrations by receiving supply of electrical energy, in which when, in a cross-section intersecting the central axis (L) at right angles, a virtual polygon (P) formed by connecting together virtual points (P1) separated by a predetermined distance (d2) from the central axis (L) and a first virtual distance (d1) between the central axis (L) and each side (P2) of the virtual polygon (P) are defined, the casing (15) includes, in the cross-section intersecting the central axis (L) at right angles, circular arc portions (31) forming circular arc shapes about the central axis (L) and having, as a distance (r) from the central axis (L), a first length greater than the first virtual distance (d1) but smaller than the predetermined distance (d2), and extension portions (35) extending outward relative to the circular arc portions (31) at the same positions as the virtual points (P1) as viewed about the central axis (L) and having, as a distance (d) from the central axis (L), a second length (d) greater than the first length (r) but not greater than the predetermined distance (d2).

The disclosed technology is not limited to the embodiments and modifications described hereinbefore, and various modifications are possible in practice within a scope not departing from the spirit of the disclosed technology. Further, the individual embodiments and modifications may be practiced in combination as much as possible as needed, and in such cases, combined advantageous effects can be brought about. Furthermore, inventions of various levels are included in the embodiments and modifications described hereinbefore, and a variety of inventions can be derived by appropriate combinations of the plural features disclosed herein.

In sum, one aspect of the disclosed technology is directed to a transducer unit used in a treatment instrument that comprises an ultrasonic transducer configured to generate ultrasonic vibrations when receiving supply of electrical energy. A cylindrically-shaped casing is configured to hold the ultrasonic transducer therein along a central axis from a distal end to a proximal end. The cylindrically-shaped casing includes an outer circumferential portion having respective circular arc portions and extension portions formed thereon. A virtual polygon is formed by connecting together a plurality of virtual points located at positions outside of the outer circumferential portion and is separated by a predetermined distance from the central axis when a cross-section intersecting the central axis at right angles and a first virtual distance between the central axis and each side of the virtual polygon are defined. The circular arc portions each includes, as a radius from the central axis, a first length greater than the first virtual distance but smaller than the predetermined distance. The extension portions extend at the positions of the virtual points, respectively, over a second length, which is greater than the first length but is smaller than the predetermined distance, as a distance from the central axis. The first length is smaller in terms of the distance from the central axis on a side of the proximal end than on a side of the distal end.

At least a portion of the cylindrically-shaped casing is formed over an entire circumference about the central axis by the circular arc portions and the extension portions. The extension portions are disposed extending along the central axis. The extension portions each extend over a predetermined length relative to the circular arc portions and wherein the predetermined length becomes smaller from one end toward an opposite end of the cylindrically-shaped casing. The cylindrically-shaped casing has a greater wall thickness at the extension portions than at the circular arc portions. The extension portions and the circular arc portions are alternately arranged about the central axis on an outer circumferential surface of the cylindrically-shaped casing. In the transducer unit the virtual polygon is a regular hexagon. The cylindrically-shaped casing further includes at least one projection protruding outwardly therefrom. The projection extends in parallel with respect to the central axis. The projection extends in a circumferential direction of the cylindrically-shaped casing. The cylindrically-shaped casing further includes a plurality of projections protruding outwardly therefrom.

Another aspect of the disclosed technology is directed to a transducer unit used in a treatment instrument that comprises an ultrasonic transducer configured to generate ultrasonic vibrations when receiving supply of electrical energy. A cylindrically-shaped casing is configured to hold the ultrasonic transducer therein along a central axis from a distal end to a proximal end. The cylindrically-shaped casing includes an inner circumference and an outer circumference. The inner circumference includes at least a portion formed from a side of the distal end to a side of the proximal end with a predetermined radius from the central axis when a cross-section intersecting the central axis at right angles. The outer circumference is formed from parts of a polygon with an inscribed circle having a radius of the inner circumference and from parts of a circumference having a greater radius from the central axis on the side of the distal end than on the side of the proximal end. The outer circumference is formed from sides of the polygon if a distance from the central axis to each side of the polygon is greater than the radius of the circumference. The outer circumference is formed from circular arc portions of the circumference if the distance from the central axis to each side of the polygon is not greater than the radius of the circumference.

A further aspect of the disclosed technology is directed to an ultrasonic treatment instrument that comprises a transducer unit having an ultrasonic transducer configured to generate ultrasonic vibrations using supply of electrical energy. The cylindrically-shaped casing to hold the ultrasonic transducer therein along a central axis from a distal end to a proximal end. A treatment unit having an end effector is configured to receive the ultrasonic vibrations. The cylindrically-shaped casing includes an outer circumferential portion having respective circular arc portions and extension portions formed thereon. A virtual polygon is formed by connecting together a plurality of virtual points located at positions outside of the outer circumferential portion and is separated by a predetermined distance from the central axis when a cross-section intersecting the central axis at right angles and a first virtual distance between the central axis and each side of the virtual polygon are defined. The circular arc portions each includes, as a radius from the central axis, a first length greater than the first virtual distance but smaller than the predetermined distance. The extension portions extend at the positions of the virtual points, respectively, over a second length, which is greater than the first length but is smaller than the predetermined distance, as a distance from the central axis. The first length is smaller in terms of the distance from the central axis on a side of the proximal end than on a side of the distal end.

While various embodiments of the disclosed technology have been described above, it should be understood that they have been presented by way of example only, and not of limitation. Likewise, the various diagrams may depict an example schematic or other configuration for the disclosed technology, which is done to aid in understanding the features and functionality that can be included in the disclosed technology. The disclosed technology is not restricted to the illustrated example schematic or configurations, but the desired features can be implemented using a variety of alternative illustrations and configurations. Indeed, it will be apparent to one of skill in the art how alternative functional, logical or physical locations and configurations can be implemented to implement the desired features of the technology disclosed herein.

Although the disclosed technology is described above in terms of various exemplary embodiments and implementations, it should be understood that the various features, aspects and functionality described in one or more of the individual embodiments are not limited in their applicability to the particular embodiment with which they are described, but instead can be applied, alone or in various combinations, to one or more of the other embodiments of the disclosed technology, whether or not such embodiments are described and whether or not such features are presented as being a part of a described embodiment. Thus, the breadth and scope of the technology disclosed herein should not be limited by any of the above-described exemplary embodiments.

Terms and phrases used in this document, and variations thereof, unless otherwise expressly stated, should be construed as open ended as opposed to limiting. As examples of the foregoing: the term "including" should be read as meaning "including, without limitation" or the like; the term "example" is used to provide exemplary instances of the item in discussion, not an exhaustive or limiting list thereof; the terms "a" or "an" should be read as meaning "at least one," "one or more" or the like; and adjectives such as "conventional," "traditional," "normal," "standard," "known" and terms of similar meaning should not be construed as limiting the item described to a given time period or to an item available as of a given time, but instead should be read to encompass conventional, traditional, normal, or standard technologies that may be available or known now or at any time in the future. Likewise, where this document refers to technologies that would be apparent or known to one of ordinary skill in the art, such technologies encompass those apparent or known to the skilled artisan now or at any time in the future.

The presence of broadening words and phrases such as "one or more," "at least," "but not limited to" or other like phrases in some instances shall not be read to mean that the narrower case is intended or required in instances where such broadening phrases may be absent.

Additionally, the various embodiments set forth herein are described in terms of exemplary schematics, block diagrams, and other illustrations. As will become apparent to one of ordinary skill in the art after reading this document, the illustrated embodiments and their various alternatives can be implemented without confinement to the illustrated examples. For example, block diagrams and their accompanying description should not be construed as mandating a particular configuration.

What is claimed is:

1. A transducer unit used in a treatment instrument, comprising:
    an ultrasonic transducer configured to generate ultrasonic vibrations when receiving supply of electrical energy; and
    a cylindrically-shaped casing configured to hold the ultrasonic transducer therein along a central axis from a distal end to a proximal end wherein
    the cylindrically-shaped casing includes an outer circumferential portion having respective circular arc portions and extension portions formed thereon and wherein
    a virtual polygon formed by connecting together a plurality of virtual points located at positions outside of the outer circumferential portion and being separated by a predetermined distance from the central axis when a cross-section intersecting the central axis at right angles and a first virtual distance between the central axis and each side of the virtual polygon are defined,
    the circular arc portions each includes, as a radius from the central axis, a first length greater than the first virtual distance but smaller than the predetermined distance,
    the extension portions extend at the positions of the virtual points, respectively, over a second length, which is greater than the first length but is smaller than the predetermined distance, as a distance from the central axis, and
    the first length is smaller in terms of the distance from the central axis on a side of the proximal end than on a side of the distal end, the first length continuously increasing from the proximal end to the distal end.

2. The transducer unit of claim 1, wherein
    at least a portion of the cylindrically-shaped casing is formed over an entire circumference about the central axis by the circular arc portions and the extension portions.

3. The transducer unit of claim 1, wherein
    the extension portions are disposed extending along the central axis.

4. The transducer unit of claim 3, wherein
    the extension portions each extend over a predetermined length relative to the circular arc portions and wherein the predetermined length becomes smaller from one end toward an opposite end of the cylindrically-shaped casing.

5. The transducer unit of claim 1, wherein
    the cylindrically-shaped casing has a greater wall thickness at the extension portions than at the circular arc portions.

6. The transducer unit of claim 1, wherein
    the extension portions and the circular arc portions are alternately arranged about the central axis on an outer circumferential surface of the cylindrically-shaped casing.

7. The transducer unit of claim 1, wherein
    the virtual polygon is a regular hexagon.

8. The transducer unit of claim 1, wherein
    the cylindrically-shaped casing further includes at least one projection protruding outwardly therefrom.

9. The transducer unit of claim 8, wherein
    the projection extends in parallel with respect to the central axis.

10. The transducer unit of claim 8, wherein
    the projection extends in a circumferential direction of the cylindrically-shaped casing.

11. The transducer unit of claim 8, wherein
    the cylindrically-shaped casing further includes a plurality of projections protruding outwardly therefrom.

12. The transducer unit of claim 1, wherein
    at substantially a same angular position about the central axis, a difference from the second length to the first length is continuously smaller from the proximal end to the distal end.

13. A transducer unit used in a treatment instrument, comprising:
    an ultrasonic transducer configured to generate ultrasonic vibrations when receiving supply of electrical energy; and
    a cylindrically-shaped casing configured to hold the ultrasonic transducer therein along a central axis from a distal end to a proximal end, wherein
    the cylindrically-shaped casing includes an inner circumference and an outer circumference,
    the inner circumference includes at least a portion formed from a side of the distal end to a side of the proximal end with a predetermined radius from the central axis when a cross-section intersecting the central axis at right angles, and
    the outer circumference being formed from parts of a polygon with an inscribed circle having a radius of the inner circumference, and from parts of a circumference having a greater radius from the central axis on the side of the distal end than on the side of the proximal end, a radius of the parts of the circumference continuously increasing from the proximal end to the distal end, and
    the outer circumference being formed from sides of the polygon if a distance from the central axis to each side of the polygon is greater than the radius of the circumference, or
    the outer circumference being formed from circular arc portions of the circumference if the distance from the central axis to each side of the polygon is not greater than the radius of the circumference.

14. An ultrasonic treatment instrument comprising:
    a transducer unit having an ultrasonic transducer configured to generate ultrasonic vibrations using supply of electrical energy, and a cylindrically-shaped casing to hold the ultrasonic transducer therein along a central axis from a distal end to a proximal end; and a treatment unit having an end effector configured to receive the ultrasonic vibrations and wherein
the cylindrically-shaped casing includes an outer circumferential portion having respective circular arc portions and extension portions formed thereon,
a virtual polygon formed by connecting together a plurality of virtual points located at positions outside of the outer circumferential portion and being separated by a predetermined distance from the central axis when a cross-section intersecting the central axis at right angles and a first virtual distance between the central axis and each side of the virtual polygon are defined,
the circular arc portions each includes, as a radius from the central axis, a first length greater than the first virtual distance but smaller than the predetermined distance,
the extension portions extend at the positions of the virtual points, respectively, over a second length, which is greater than the first length but is smaller than the predetermined distance, as a distance from the central axis, and
the first length is smaller in terms of the distance from the central axis on a side of the proximal end than on a side of the distal end, the first length continuously increasing from the proximal end to the distal end.

* * * * *